(12) United States Patent
Dhyllon

(10) Patent No.: US 10,258,553 B1
(45) Date of Patent: Apr. 16, 2019

(54) HAIR STRENGTHENING CONDITIONER FORMULATION WITH REDUCED COST, EASY FORMULATION AND IMPROVED PERFORMANCE

(71) Applicant: Amen Dhyllon, Wynnewood, PA (US)

(72) Inventor: Amen Dhyllon, Wynnewood, PA (US)

(73) Assignee: SERENDIPITY TECHNOLOGIES LLC., Wynnewood, PA (US)

( * ) Notice: Subject to any disclaimer, the term of this patent is extended or adjusted under 35 U.S.C. 154(b) by 0 days.

(21) Appl. No.: 16/132,645

(22) Filed: Sep. 17, 2018

(51) Int. Cl.
| | | |
|---|---|---|
| *A61K 8/34* | (2006.01) |
| *A61K 8/37* | (2006.01) |
| *A61K 8/41* | (2006.01) |
| *A61K 8/55* | (2006.01) |
| *A61K 8/65* | (2006.01) |
| *A61K 8/73* | (2006.01) |
| *A61Q 5/12* | (2006.01) |

(52) U.S. Cl.
CPC .............. *A61K 8/342* (2013.01); *A61K 8/345* (2013.01); *A61K 8/347* (2013.01); *A61K 8/37* (2013.01); *A61K 8/416* (2013.01); *A61K 8/553* (2013.01); *A61K 8/65* (2013.01); *A61K 8/731* (2013.01); *A61Q 5/12* (2013.01); *A61K 2800/5426* (2013.01)

(58) Field of Classification Search
CPC combination set(s) only.
See application file for complete search history.

(56) References Cited

U.S. PATENT DOCUMENTS

| | | |
|---|---|---|
| 4,753,793 A | 6/1988 | Walton |
| 5,037,632 A | 8/1991 | Gross et al. |

FOREIGN PATENT DOCUMENTS

| | | |
|---|---|---|
| EP | 0034190 A1 | 2/1980 |
| EP | 0138395 A2 | 9/1984 |

*Primary Examiner* — Hasan S Ahmed
(74) *Attorney, Agent, or Firm* — Adam Warwick Bell; Matthew Rupert Kaser

(57) ABSTRACT

A hair strengthening conditioner formulation for application to human or animal hair for the purpose of strengthening and improving the hair. The present invention is for external application but may also be used in combination with dietary supplement compositions. The present hair strengthening conditioner comprises a proprietary mixture of a number of compounds as described in the tables and the claims.

6 Claims, No Drawings

HAIR STRENGTHENING CONDITIONER FORMULATION WITH REDUCED COST, EASY FORMULATION AND IMPROVED PERFORMANCE

FIELD OF THE INVENTION

The embodiments of the present invention relate to a preparation for application to human or animal hair for the purpose of strengthening and improving the hair. The present invention is for external application but may also be used in combination with dietary supplement compositions. The invention provides a hair strengthening conditioner formulation with reduced cost, easy formulation and improved performance.

BACKGROUND AND PRIOR ART

Hair conditioners can be delivered from rinse-off shampoo, conditioner, treatment, and leave-on conditioning products. Similarly, skin or scalp moisturizing benefit can be delivered from either rinse-off or leave-on products.

The prior art includes compositions used for the purpose of strengthening and improving the hair. this treatment makes the hair stronger and more manageable. Conditioning products usually comprise an aqueous solution of a cationic quaternary ammonium compound, for example cetyltrimethylammonium chloride.

WO2016052834A1 discloses a cosmetic composition for hair strengthening. The cosmetic composition for hair strengthening according to the present invention can increase the hair thickness, leading to voluminous hair, by containing, as an active ingredient, a *Rhodiola sachalinensis* extract, a *Galla rhois* extract, or ursolic acid.

EP application No. 80 100 731.1 (publication No. 0 034 190; Helene Curtis Industries, Inc.) relates to hair conditioning rinse compositions having hair holding properties. These comprise an aqueous composition containing from about 0.02 to about 2 weight percent of a water-soluble anionic polymer and from about 0.1 to about 5 weight percent of a cationic surfactant capable of forming a water-insoluble reaction product with the anionic polymer.

Japanese Patent Application No. 57126-409 (Kao Soap KK) describes a hair rinse conditioner having hair setting qualities. These compositions comprise 0.1 to 10 weight percent of a quaternary ammonium salt, 0.1 to 5 weight percent of a polymer having a cationic radical of ring structure (e.g. poly(dimethyldiallylammonium chloride)) and 0.1 to 30 weight percent of an oily compound consisting of a hydrocarbon, higher alcohol or a silicone.

A hair rinse conditioner comprising a water-soluble copolymer of vinyl pyrollidone and dimethylaminoethyl methacrylate and a cationic surfactant is described in Example 13 of UK Patent Application No. 78 26346 (Publication No. 2 000 026; GAF Corporation).

The inclusion of a water-soluble polymer as described in the above Japanese and UK patent applications, respectively, has a limited effect since the polymer would be substantially rinsed out with the rinsing of the hair. Such disadvantage is referred to in the above European application.

UK Patent Application No. 2 114 580 (L'Oreal) describes a composition suitable for treating the hair, nails and/or skin, which comprises, in an appropriate medium, at least one cationic polymer of the polyamine, polyaminoamide or poly-(quaternary ammonium) type containing amine or ammonium groups in the polymer chain or joined thereto, and at least one anionic latex which is in the form of a colloidal suspension of particles of polymers containing anionic functional groups, in an aqueous or organic liquid phase. Embodiments of such a composition in the form of a rinse-off conditioner are described in Examples 1 and 2 of the application.

Various prior art compositions employ water-insoluble film-forming polymers such as latex emulsions. Examples of suitable polymer types are poly (vinyl acetate), copolymers of styrene and alkyl acrylates, and copolymers of vinyl acetate and acrylic acid. These polymers are available commercially in the form of lattices, which usually have a solids content of about 50% by weight. The size of the polymer particles in such a latex usually ranges from about 0.1 micron to about 5 microns.

Other optional ingredients which may be included in hair conditioners include hydrocarbon oils or waxes, silicones, pearlising agents, preservatives, perfumes and colourants.

The invention will now be illustrated by the following Examples. Percentages are by weight.

SUMMARY OF THE INVENTION

The invention provides a hair strengthening conditioner formulation with reduced cost, easy formulation and improved performance.

The invention provides a hair strengthening conditioner formulation for application to human or animal hair for the purpose of strengthening and improving the hair. The present invention is for external application but may also be used in combination with dietary supplement compositions. The present hair strengthening conditioner comprises a proprietary mixture of a number of compounds as described in the tables and the claims. The composition of the present invention can provide improved cosmetic conditioning benefits, especially when applied in hair shampoos, conditioners, treatments or skin cleansing products as a silicone alternative. These and other features, aspects, and advantages of the present invention will become better understood from a reading of the following description, and appended claims.

DETAILED DESCRIPTION

The invention encompasses effective and reliable conditioner for strengthening hair, and for improving the general condition and manageability of hair with reduced cost, easy formulation and improved performance.

The formulation is water-based and includes a combination of several or all of the following ingredients: Cetyl Alcohol, Olivem, Bee's Wax, CCTG (Capric TriGlyceride), Cetrimide, HEC (hydroxy-ethylcellulose), Glycerin, Kara base, T-20 (a surfactant), PG (Propylene glycol), EDTA, Sodium Benzoate, Phenoxy, Coconut Oil, Argon Oil, Jojoba Oil, Curry leaf Extract, Beetroot Extract. Diasleek-802, Karacyne, DC-245 (a Silicone fluid), Soya Lecithin, Collagen, Biotin, Cetrimonium Chloride, Fragrance Coconut Milk, D Penthanol, G-700 (a Sunscreen), Vitamin E, Vitamin B-3, Amaport and CAPB.

Other ingredients and additives may include, for example, cosmetic conditioning oils, cetyl ethylhexanoate, oil thickeners such as dextrin palmitate, and additional components selected from the group consisting of oleyl erucate, hydrogenated polyisobutene, PPG-3 caprylyl ether, vitamin E, panthenol, panthenyl ethyl ether, plant extracts, vitamins and nutrients.

The hair strengthening conditioner may be formulated in a number of ways using a number of non-active ingredients, carriers, fillers and fragrances and consistency enhancers. The composition of the present invention may include other additional components, which may be selected according to the desired characteristics of the final composition and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other hair conditioning oils such as oleyl erucate with a trade name of Cetiol J 600 available from Cognis, part of BASF, hydrogenated polyisobutene with a trade name of ParLeam available from NOF, PPG-3 caprylyl ether with a trade name of Sofcare GP-1 from Kao Chemical; scalp care ingredients such as vitamin E with tradename Emix-d available from Eisai, panthenol available from Roche, panthenyl ethyl ether available from Roche, plant extracts, and nutrients.

Method of Preparation

The elements may be combined at room temperature and mixed and homogenized using a conventional stirrer or mixer. In other embodiments, the elements may be combined at an elevated temperature. The elements may include water, Cetyl Alcohol, Olivem, Bee's Wax, CCTG (Capric TriGlyceride), Cetrimide, HEC (hydroxy-ethylcellulose), Glycerin, Kara base, T-20 (a surfactant), PG (Propylene glycol), EDTA, Sodium Benzoate, Phenoxy, Coconut Oil, Argon Oil, Jojoba Oil, Curry leaf Extract, Beetroot Extract, Diasleek-802, Karacyne, DC-245 (a Silicone fluid), Soya Lecithin, Collagen, Biotin, Cetrimonium Chloride, Fragrance Coconut Milk, D Penthanol, G-700 (a Sunscreen), Vitamin E, Vitamin B-3, Amaport and CAPB. In certain embodiments the oil ingredients and other ingredients are heated to 85-90 degrees Celsius, oil thickener is then added and mixed into the oil with agitation and the mixture may be maintained at a temperature of 85-90 degrees Celsius until the components are homogenized, and no solids are observed. When included, other additional components are added with agitation. The mixture is then slowly cooled to room temperature. The mixtures obtained can be then added into hair care or skin care products such as shampoos and body soaps. The mixtures can be added directly or as a pre-emulsified emulsion using anionic, nonionic, or cationic surfactants as an emulsifier.

When applied in hair care or skin care products, the embodiments disclosed have many advantages. For example, they are especially suitable for strengthening the hair.

Furthermore, another very important advantage is that that the price of the finished product is less than that of conventional formulations.

One object of the present invention is to provide effective and reliable conditioner for strengthening hair, and for improving the general condition and manageability of hair. The formulation of the invention is cheaper to create than that of the conventional commercial formulations, yet it provides improved quality.

Each of the embodiments is broken down into three examples, infra. The first example is a list of the ingredients with no set quantities. However, it will be clear that any quantities provided will be those that are practical and consistent with customary human consumption. Another example is the ranges of the quantities of the ingredients with a 20%+/− variation, i.e., with a variance of 20% more or less of each ingredient. In other embodiments, the variation may be plus or minus 5%, 10%, 15%, 25%, 30%, 35%, 40%, 50%, 60% or 75% by weight. Indeed, in certain embodiments, the amount of any particular ingredient may be several times that shown, for example twice, three times, 5 times or ten times that shown in the examples. A further example is the optimum quantities of the ingredients. Other non-enumerated ingredients may also be present. Note that in alternative embodiments the invention may encompass a formulation consisting essentially of a combination of any of the listed active components, but not including any other active components. These formulations may include non-active ingredients such as fillers and carriers, scent enhancers, perfumes, pearlizing agents, etc.

EXAMPLES

The below examples show different formulations. Formulations 1 and 2 include the essential ingredients. Formulations 3 and 4 include essential and desirable ingredients, Formulations 5 and 6 include essential, desirable and optional ingredients. Formulation 6 shows an example of a fully costed product, which is lower in cost than presently-available products of the same type.

| Formulation 1 and Formulation 2 | | |
|---|---|---|
| Ingredients | Formulation 1 | Formulation 2 |
| Water | Balance to make 100% | Balance (71.250%) |
| Cetyl Alcohol | 4-6% | 5.000% |
| PEG-free emulsifier | 0.8-1.2% | 1.000% |
| capric/caprylic triglyceride | 2-3% | 2.500% |
| Cetrimide | 0.8-1.2% | 1.000% |
| hydroxyethyl cellulose | 0.2-0.4% | 0.300% |
| Glycerin | 0.7-1.3% | 1.500% |
| Polyoxyethylenesorbitan monolaurate | 0.5-0.9% | 0.750% |
| Propylene glycol | 0.4-0.6% | 0.500% |
| EDTA | 0.08-0.12% | 0.100% |
| Sodium Benzoate | 0.1-0.3% | 0.200% |
| Phenoxy | 0.1-0.3% | 0.200% |
| A cationic polymer (such as polyquaternium-73) | 0.7-1.3% | 1.200% |
| Soya Lecithin | 0.1-0.3% | 0.200% |
| Collagen | 0.1-0.3% | 0.200% |
| Cetrimonium Chloride | 0.4-0.6% | 0.500% |

| Formulation 3 and Formulation 4 | | |
|---|---|---|
| Ingredients | Formulation 3 | Formulation 4 |
| Water | Balance to make 100% | Balance (71.250%) |
| Cetyl Alcohol | 4-6% | 5.000% |
| PEG-free emulsifier | 0.8-1.2% | 1.000% |
| Bee's Wax | 0.2-0.6% | 0.400% |
| capric/caprylic triglyceride | 2-3% | 2.500% |
| Cetrimide | 0.8-1.2% | 1.000% |
| hydroxyethyl cellulose | 0.2-0.4% | 0.300% |
| Glycerin | 0.7-1.3% | 1.500% |
| a base conditioner | 1-3% | 2.000% |
| Polyoxyethylenesorbitan monolaurate | 0.5-0.9% | 0.750% |
| Propylene glycol | 0.4-0.6% | 0.500% |
| EDTA | 0.08-0.12% | 0.100% |
| Sodium Benzoate | 0.1-0.3% | 0.200% |
| Phenoxy | 0.1-0.3% | 0.200% |
| Argon Oil | 0.1-0.3% | 0.200% |
| Curry leaf Extract | 0.2-0.4% | 0.300% |
| Beetroot Extract | 0.1-0.3% | 0.200% |
| A cationic polymer (such as polyquaternium-73) | 0.7-1.3% | 1.200% |

| Formulation 3 and Formulation 4 | | |
| --- | --- | --- |
| Ingredients | Formulation 3 | Formulation 4 |
| Keratin-derived protein e.g., Karacyne | 0.1-0.3% | 0.200% |
| DC-245 | 0.5-0.9% | 0.750% |
| Soya Lecithin | 0.1-0.3% | 0.200% |
| Collagen | 0.1-0.3% | 0.200% |
| Cetrimonium Chloride | 0.4-0.6% | 0.500% |
| Penthanol | 0.1-0.3% | 0.200% |
| G-700 | 0.4-0.6% | 0.500% |
| CAPB | 5-7% | 6.000% |

| Formulation 4 and Formulation 5 | | |
| --- | --- | --- |
| Ingredients | Formulation 4 | Formulation 5 |
| Water | Balance to make 100% | Balance (71.250%) |
| Cetyl Alcohol | 4-6% | 5.000% |
| PEG-free emulsifier (such as Olivem) | 0.8-1.2% | 1.000% |
| Bee's Wax | 0.2-0.6% | 0.400% |
| capric/caprylic triglyceride | 2-3% | 2.500% |
| Cetrimide | 0.8-1.2% | 1.000% |
| hydroxyethyl cellulose | 0.2-0.4% | 0.300% |
| Glycerin | 0.7-1.3% | 1.500% |
| A base conditioner | 1-3% | 2.000% |
| Polyoxyethylenesorbitan monolaurate | 0.5-0.9% | 0.750% |
| Propylene glycol | 0.4-0.6% | 0.500% |
| EDTA | 0.08-0.12% | 0.100% |
| Sodium Benzoate | 0.1-0.3% | 0.200% |
| Phenoxy | 0.1-0.3% | 0.200% |
| Coconut Oil | 0.7-1.3% | 1.500% |
| Argon Oil | 0.1-0.3% | 0.200% |
| Jojoba Oil | 0.1-0.3% | 0.200% |
| Curry leaf Extract | 0.2-0.4% | 0.300% |
| Beetroot Extract | 0.1-0.3% | 0.200% |
| A cationic polymer (such as polyquaternium-73) | 0.7-1.3% | 1.200% |
| Keratin-derived protein e.g., Karacyne | 0.1-0.3% | 0.200% |
| DC-245 | 0.5-0.9% | 0.750% |
| Soya Lecithin | 0.1-0.3% | 0.200% |
| Collagen | 0.1-0.3% | 0.200% |
| Biotin | 0.04-0.06% | 0.050% |
| Cetrimonium Chloride | 0.4-0.6% | 0.500% |
| Fragrance of Coconut Milk | 0.3-0.5% | 0.400% |
| Penthanol | 0.1-0.3% | 0.200% |
| G-700 | 0.4-0.6% | 0.500% |
| Vitamin E | 0.08-0.12% | 0.100% |
| Vitamin B-3 | 0.08-0.12% | 0.100% |
| A herbal extract such as Amaport | 0.08-0.12% | 0.100% |
| CAPB | 5-7% | 6.000% |

| Formulation 6 - showing the costed product | | | | |
| --- | --- | --- | --- | --- |
| No. | Ingredient | Percentage | Price/Kg | Total |
| 1 | Water | 71.250% | 3.000 | 2.1375 |
| 2 | Cetyl Alcohol | 5.000% | 125.000 | 6.2500 |
| 3 | PEG-free emulsifier (such as Olivem) | 1.000% | 1730.000 | 17.3000 |
| 4 | Bees' Wax | 0.400% | 265.000 | 1.0600 |
| 5 | capric/caprylic triglyceride | 2.500% | 475.000 | 11.8750 |
| 6 | cetrimide | 1.000% | 900.000 | 9.0000 |
| 7 | hydroxyethyl cellulose | 0.300% | 1160.000 | 3.4800 |
| 8 | Glycerin | 1.500% | 120.000 | 1.8000 |
| 9 | Kara base | 2.000% | 1300.000 | 26.0000 |
| 10 | Polyoxyethylenesorbitan monolaurate | 0.750% | 230.000 | 1.7250 |
| 11 | Propylene glycol | 0.500% | 156.000 | 0.7800 |
| 12 | EDTA | 0.100% | 240.000 | 0.2400 |
| 13 | Sodium Benzoate | 0.200% | 130.000 | 0.2600 |
| 14 | Phenoxy | 0.200% | 245.000 | 0.4900 |
| 15 | Coconut Oil | 1.500% | 380.000 | 5.7000 |
| 16 | Argon Oil | 0.200% | 2800.000 | 5.6000 |
| 17 | Jojoba Oil | 0.200% | 1000.000 | 2.0000 |
| 18 | Curry leaf Extract | 0.300% | 780.000 | 2.3400 |
| 19 | Beetroot Extract | 0.200% | 850.000 | 1.7000 |
| 20 | A cationic polymer (such as polyquaternium-73) | 1.200% | 1750.000 | 21.0000 |
| 21 | Keratin-derived protein e.g., Karacyne | 0.200% | 10000.000 | 20.0000 |
| 22 | DC-245 | 0.750% | 520.000 | 3.9000 |
| 23 | Soya Lecithin | 0.200% | 1850.000 | 3.7000 |
| 24 | Collagen | 0.200% | 8000.000 | 16.0000 |
| 25 | Biotin | 0.050% | 23000.000 | 11.5000 |
| 26 | Cetrimonium Chloride | 0.500% | 230.000 | 1.1500 |
| 27 | Fragrance Coconut Milk | 0.400% | 1700.000 | 6.8000 |
| 28 | D Panthenol | 0.200% | 5600.000 | 11.2000 |
| 29 | G-700 | 0.500% | 80.000 | 0.4000 |
| 30 | Vitamin E | 0.100% | 900.000 | 0.9000 |
| 31 | Vitamin B-3 | 0.100% | 800.000 | 0.8000 |
| 32 | Amaport | 0.100% | 6000.000 | 6.0000 |
| 33 | CAPB | 6.000% | 78.000 | 4.6800 |
| | Total | 99.600% | 65539.000 | 207.7675 |
| | RM Cost /Piece | | | 62.3303 |

Example Showing Costed Packing Components

| Packaging | | | |
| --- | --- | --- | --- |
| 1 | 300 ml Amber Bottle | 1 | 7.5 |
| 2 | Pump Napla | 1 | 7 |
| 3 | Label Reynders | 1 | 5.5 |
| 4 | Shrink | 1 | 0.5 |
| 5 | CBB | 1 | 1.5 |
| | Total | | 22 |
| | Cost /Piece for 300 ml | | |

The above components may be present as variants or salts thereof or may be compounded with various other components such as carriers, fillers, oils, emulsifiers. They may be present in solid, powder or liquid form.

While the embodiments of the present invention have been illustrated and described in the examples, the invention is not meant to be limited by the examples and the meets and bounds of some of the embodiments of the invention is set out in the claims.

TERMS AND DEFINITIONS

Water=$H_2O$ which may include de-minimus amounts of salts, carbonates, metals or other typical components.

Cetyl Alcohol=Cetyl alcohol, also known as hexadecan-1-ol and palmityl alcohol, is a fatty alcohol with the formula CH315OH. At room temperature, cetyl alcohol takes the form of a waxy white solid or flakes. The name cetyl derives from the whale oil from which it was first isolated.

OLIVEM®=a white to ivory waxy flake solid. It is a PEG-free co-emulsifier, self-emulsifying multifunctional ingredient, HLB 8-9, that is COSMOS-validated Bee's Wax=Beeswax (cera alba) is a natural wax produced by honey bees of the genus Apis. The wax is formed into "scales" by eight wax-producing glands of bees.

CCTG=Capric/caprylic triglyceride is a combined tri-ester, a blend of capric and caprylic acids. It is also known as fractionated coconut oil.

Cetrimide=Cetrimide is an antiseptic which is a mixture of different quaternary ammonium salts including cetrimonium bromide. It was first discovered and developed by ICI and introduced under the brand name Cetavlon. It is used as a 1-3% solution for cleaning roadside accident wounds.

HEC=Hydroxyethyl cellulose, also known by the trade name NATROSOL®, is a gelling and thickening agent derived from cellulose. It is widely used in cosmetics, cleaning solutions, and other household products.

Glycerin=Glycerol is a simple polyol compound. It is a colorless, odorless, viscous liquid that is sweet-tasting and non-toxic. The glycerol backbone is found in all lipids known as triglycerides. It is widely used in the food industry as a sweetener and humectant and in pharmaceutical formulations. Glycerol has three hydroxyl groups that are responsible for its solubility in water and its hygroscopic nature.

Kara base=a hair conditioning agent or a "base conditioner". In this disclosure, it should be understood that Kara base is optional and can be left out of any formulation or replaced with any base conditioner or with any other generic formulation used as a hair conditioning agent.

Base conditioner=any base conditioner commercially available which have ingredients of, for example, Aqua, Cetearyl Alcohol, Glycerine, Phenoxyethanol, Distearoylethyl Dimonium Chloride, Behentrimonium Chloride, Panthenol, Isopropyl Alcohol, Hydrolysed Sweet Almond Seedcake T-20=Tween 20 is oil-in-water emulsifier, can be used as solvent, diffusant, stabilizer, lubricant and anti-static agent etc.

TWEEN® 20=Polyethylene glycol sorbitan monolaurate, Polyoxyethylenesorbitan monolaurate PG=Propylene glycol (IUPAC name: propane-1,2-diol) is a synthetic organic compound with the chemical formula $C_3H_8O_2$. It is a viscous, colorless liquid.

EDTA=ethylenediaminetetraacetic acid (EDTA) is a calcium chelating agent

Sodium Benzoate=Sodium benzoate is a substance which has the chemical formula $NaC_7H_5O_2$. It is a widely used food preservative, with an E number of E211.

Phenoxy=a preservative (a "procrastinator"), used in trace amounts.

Coconut Oil=Coconut oil, or copra oil, is an edible oil extracted from the kernel or meat of mature coconuts harvested from the coconut palm.

Argon Oil=Argan oil is a plant oil produced from the kernels of the argan tree (*Argania spinosa* L.)

Jojoba Oil=Jojoba is the liquid produced in the seed of the *Simmondsia chinensis* plant, Curry leaf Extract=the extract of the curry tree which is a tropical to sub-tropical tree in the family Rutaceae, which is native to India and Sri Lanka Beetroot Extract=extract of *Beta vulgaris* or related species DIASLEEK®-802=polyquaternium-73 is a cationic polymer preparation and is a silicone compound to prevent dryness in hair and scalp.

Karacyne=a keratin-derived protein

DC-245=Cytopentosyloxane, which is a Silicone fluoride substance used as a conditioning agent Soya Lecithin=an amphiphilic extract of soy Collagen=animal protein found in connective tissue G-700=a surfactant, foaming agent and sunscreen agent CABP=cocamidopropyl betaine (an amphoteric surfactant)

Amaport=a herbal extract with properties that interact with or change physiological or chemical properties of another compound Water: Although water is described in the tables as "Balance to make 100%" or as a given percentage, it must be understood that the percentages in the formulations do not always add up to 100% and that in various formulations additional non-listed ingredients may be added and used. Thus, the amount of water may be added as needed, and may not provide the entire balance of any particular formulation. For example, water may be present in amounts from 1% to 95%, from 5% to 90% or from 5% to 75% or any other percentage.

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixture" is meant to include a simple combination of materials and any compounds that may result from their combination.

The invention claimed is:

1. A hair conditioner preparation for strengthening the hair, the preparation comprising, in the following proportions, the following:

| Water | As required |
|---|---|
| Cetyl Alcohol | 4-6% |
| PEG-free emulsifier | 0.8-1.2% |
| capric/caprylic triglyceride | 2-3% |
| Cetrimide | 0.8-1.2% |
| hydroxyethyl cellulose | 0.2-0.4% |
| Glycerin | 0.7-1.3% |
| Polyoxyethylenesorbitan monolaurate | 0.5-0.9% |
| Propylene glycol | 0.4-0.6% |
| EDTA | 0.08-0.12% |
| Sodium Benzoate | 0.1-0.3% |
| Phenoxy | 0.1-0.3% |
| A cationic polymer | 0.7-1.3% |
| Soya Lecithin | 0.1-0.3% |
| Collagen | 0.1-0.3% |
| Cetrimonium Chloride | 0.4-0.6%. |

2. The formulation of claim 1 comprising:

| Water | As required |
|---|---|
| Cetyl Alcohol | 5.000% |
| PEG-free emulsifier | 1.000% |

| Water | As required |
|---|---|
| capric/caprylic triglyceride | 2.500% |
| Cetrimide | 1.000% |
| hydroxyethyl cellulose | 0.300% |
| Glycerin | 1.500% |
| Polyoxyethylenesorbitan monolaurate | 0.750% |
| Propylene glycol | 0.500% |
| EDTA | 0.100% |
| Sodium Benzoate | 0.200% |
| Phenoxy | 0.200% |
| A cationic polymer | 1.200% |
| Soya Lecithin | 0.200% |
| Collagen | 0.200% |
| Cetrimonium Chloride | 0.500%. |

3. The formulation of claim 1 comprising:

| Water | As required |
|---|---|
| Cetyl Alcohol | 4-6% |
| PEG-free emulsifier | 0.8-1.2% |
| Bee's Wax | 0.2-0.6% |
| capric/caprylic triglyceride | 2-3% |
| Cetrimide | 0.8-1.2% |
| hydroxyethyl cellulose | 0.2-0.4% |
| Glycerin | 0.7-1.3% |
| a base conditioner | 1-3% |
| Polyoxyethylenesorbitan monolaurate | 0.5-0.9% |
| Propylene glycol | 0.4-0.6% |
| EDTA | 0.08-0.12% |
| Sodium Benzoate | 0.1-0.3% |
| Phenoxy | 0.1-0.3% |
| Argon Oil | 0.1-0.3% |
| Curry leaf Extract | 0.2-0.4% |
| Beetroot Extract | 0.1-0.3% |
| A cationic polymer | 0.7-1.3% |
| Keratin-derived protein | 0.1-0.3% |
| DC-245 | 0.5-0.9% |
| Soya Lecithin | 0.1-0.3% |
| Collagen | 0.1-0.3% |
| Cetrimonium Chloride | 0.4-0.6% |
| Panthenol | 0.1-0.3% |
| G-700 | 0.4-0.6% |
| cocamidopropyl betaine | 5-7%. |

4. The formulation of claim 3 comprising:

| Water | As required |
|---|---|
| Cetyl Alcohol | 5.000% |
| PEG-free emulsifier | 1.000% |
| Bee's Wax | 0.400% |
| capric/caprylic triglyceride | 2.500% |
| Cetrimide | 1.000% |
| hydroxyethyl cellulose | 0.300% |
| Glycerin | 1.500% |
| a base conditioner | 2.000% |
| Polyoxyethylenesorbitan monolaurate | 0.750% |
| Propylene glycol | 0.500% |
| EDTA | 0.100% |
| Sodium Benzoate | 0.200% |
| Phenoxy | 0.200% |
| Argon Oil | 0.200% |
| Curry leaf Extract | 0.300% |
| Beetroot Extract | 0.200% |
| A cationic polymer | 1.200% |
| Keratin-derived protein | 0.200% |
| DC-245 | 0.750% |
| Soya Lecithin | 0.200% |
| Collagen | 0.200% |
| Cetrimonium Chloride | 0.500% |
| Panthenol | 0.200% |
| G-700 | 0.500% |
| cocamidopropyl betaine | 6.000%. |

5. The formulation of claim 1 comprising:

| Water | As required |
|---|---|
| Cetyl Alcohol | 4-6% |
| PEG-free emulsifier | 0.8-1.2% |
| Bee's Wax | 0.2-0.6% |
| capric/caprylic triglyceride | 2-3% |
| Cetrimide | 0.8-1.2% |
| hydroxyethyl cellulose | 0.2-0.4% |
| Glycerin | 0.7-1.3% |
| A base conditioner | 1-3% |
| Polyoxyethylenesorbitan monolaurate | 0.5-0.9% |
| Propylene glycol | 0.4-0.6% |
| EDTA | 0.08-0.12% |
| Sodium Benzoate | 0.1-0.3% |
| Phenoxy | 0.1-0.3% |
| Coconut | 0.7-1.3% |
| Argon Oil | 0.1-0.3% |
| Jojoba Oil | 0.1-0.3% |
| Curry leaf Extract | 0.2-0.4% |
| Beetroot Extract | 0.1-0.3% |
| A cationic polymer | 0.7-1.3% |
| Keratin-derived protein | 0.1-0.3% |
| DC-245 | 0.5-0.9% |
| Soya Lecithin | 0.1-0.3% |
| Collagen | 0.1-0.3% |
| Biotin | 0.04-0.06% |
| Cetrimonium Chloride | 0.4-0.6% |
| Fragrance of Coconut Milk | 0.3-0.5% |
| Panthenol | 0.1-0.3% |
| G-700 | 0.4-0.6% |
| Vitamin E | 0.08-0.12% |
| Vitamin B-3 | 0.08-0.12% |
| A herbal extract | 0.08-0.12% |
| cocamidopropyl betaine | 5-7%. |

6. The formulation of claim 5 comprising:

| Water | As required |
|---|---|
| Cetyl Alcohol | 5.000% |
| PEG-free emulsifier | 1.000% |
| Bee's Wax | 0.400% |
| capric/caprylic triglyceride | 2.500% |
| Cetrimide | 1.000% |
| hydroxyethyl cellulose | 0.300% |
| Glycerin | 1.500% |
| A base conditioner | 2.000% |
| Polyoxyethylenesorbitan monolaurate | 0.750% |
| Propylene glycol | 0.500% |
| EDTA | 0.100% |
| Sodium Benzoate | 0.200% |
| Phenoxy | 0.200% |
| Coconut Oil | 1.500% |
| Argon Oil | 0.200% |
| Jojoba Oil | 0.200% |
| Curry leaf Extract | 0.300% |
| Beetroot Extract | 0.200% |
| A cationic polymer | 1.200% |
| Keratin-derived protein | 0.200% |
| DC-245 | 0.750% |
| Soya Lecithin | 0.200% |
| Collagen | 0.200% |
| Biotin | 0.050% |
| Cetrimonium Chloride | 0.500% |
| Fragrance of Coconut Milk | 0.400% |

-continued

| | |
|---|---|
| Water | As required |
| Panthenol | 0.200% |
| G-700 | 0.500% |
| Vitamin E | 0.100% |
| Vitamin B-3 | 0.100% |
| A herbal extract | 0.100% |
| cocamidopropyl betaine | 6.000%. |

* * * * *